(12) United States Patent
Gondaliya et al.

(10) Patent No.: US 12,427,127 B2
(45) Date of Patent: Sep. 30, 2025

(54) CARMUSTINE FORMULATION

(71) Applicant: EMCURE PHARMACEUTICALS LIMITED, Pune (IN)

(72) Inventors: Deepak Pragjibhai Gondaliya, Pune (IN); Hiren Pravinbhai Patel, Pune (IN); Haresh Ishwarbhai Patel, Pune (IN); Mukund Keshav Gurjar, Pune (IN)

(73) Assignee: EMCURE PHARMACEUTICALS LIMITED, Pune (IN)

( * ) Notice: Subject to any disclaimer, the term of this patent is extended or adjusted under 35 U.S.C. 154(b) by 1089 days.

(21) Appl. No.: 16/981,344

(22) PCT Filed: Mar. 30, 2019

(86) PCT No.: PCT/IB2019/052644
§ 371 (c)(1),
(2) Date: Sep. 16, 2020

(87) PCT Pub. No.: WO2019/193477
PCT Pub. Date: Oct. 10, 2019

(65) Prior Publication Data
US 2021/0361599 A1 Nov. 25, 2021

(30) Foreign Application Priority Data
Apr. 5, 2018 (IN) .............. 2018210129964

(51) Int. Cl.
| | | |
|---|---|---|
| *A61K 31/17* | (2006.01) | |
| *A61K 9/00* | (2006.01) | |
| *A61K 9/107* | (2006.01) | |
| *A61K 9/19* | (2006.01) | |
| *A61K 9/51* | (2006.01) | |
| *A61K 47/14* | (2017.01) | |
| *A61K 47/34* | (2017.01) | |
| *A61P 35/00* | (2006.01) | |

(52) U.S. Cl.
CPC .......... *A61K 31/17* (2013.01); *A61K 9/0019* (2013.01); *A61K 9/1075* (2013.01); *A61K 9/19* (2013.01); *A61K 47/14* (2013.01); *A61K 47/34* (2013.01); *A61P 35/00* (2018.01)

(58) Field of Classification Search
None
See application file for complete search history.

(56) References Cited

U.S. PATENT DOCUMENTS

| | | |
|---|---|---|
| 10,583,101 B2 | 3/2020 | Gondaliya et al. |
| 2010/0068251 A1 | 3/2010 | Ali et al. |
| 2011/0275704 A1* | 11/2011 | Troiano .................. A61K 47/34 977/773 |
| 2015/0118311 A1* | 4/2015 | Zhou .................. A61K 31/4745 514/367 |
| 2019/0298671 A1 | 10/2019 | Gondaliya et al. |

FOREIGN PATENT DOCUMENTS

| | | | |
|---|---|---|---|
| CN | 1110134 | | 10/1995 |
| CN | 1198930 A | * | 11/1998 |
| CN | 1520808 A | * | 8/2004 |
| CN | 1683016 | | 10/2005 |
| CN | 101143130 | | 3/2008 |
| CN | 101143130 A | * | 3/2008 |
| CN | 101444482 | | 6/2009 |
| CN | 102198100 | | 9/2011 |
| JP | 05221852 | | 8/1993 |
| WO | 2005072709 | | 8/2005 |
| WO | 2010132664 | | 11/2010 |
| WO | WO-2016113752 A2 | * | 7/2016 .......... A61K 31/337 |
| WO | 2018096466 | | 5/2018 |
| WO | 2019193477 | | 10/2019 |

OTHER PUBLICATIONS

Dubash, D., and U. Shah. "Water." Handbook of Pharmaceutical Excipients. 6th Edition (2009) 766-770. (Year: 2009).*
Chakroun, Rami Walid, et al. "Nanotherapeutic systems for local treatment of brain tumors." Wiley Interdisciplinary Reviews: Nanomedicine and Nanobiotechnology 10.1 (2018): e1479. (Year: 2018).*
Takenaga, Mitsuko, "Application of Lipid Microspheres for the Treatment of Cancer" Advanced Drug Delivery Reviews, vol. 20, No. Jul. 2-3, 1996, pp. 209-219 (abstract only).
PCT International Search Report for PCT/IB2017/057328, Feb. 6, 2018.
PCT Search Strategy for PCT/IB2017/057328, Feb. 6, 2018.
PCT Written Opinion of the International Searching Authority for PCT/IB2017/057328, Feb 6. 2018.
PCT International Search Report for PCT/IB2019/052644, Jun. 26, 2019.
PCT Search Strategy for PCT/IB2019/052644, Jun. 26, 2019.
PCT Written Opinion of the International Searching Authority for PCT/IB2019/052644, Jun. 26, 2019.
Kumari et al. "Nanosuspensions: A Review," International J. Pharm., 2017 7(2), 77-89.
Gossman et al., "Didodecyldimethylammonium Bromide (DMAB) Stabilized Poly(lactic-co-glycolic acid)(PLGA) Nanoparticles: Uptake and Cytotoxi Potential in Caco-2 Cells," Journal of Drug Delivery Science and Technology 43 (2018) 430-438 (available on line Nov. 6, 2017).

* cited by examiner

*Primary Examiner* — Bethany P Barham
*Assistant Examiner* — Peter Anthopolos
(74) *Attorney, Agent, or Firm* — Florek & Endres, PLLC

(57) ABSTRACT

The present invention relates to a composition comprising nitrosourea and pharmaceutically acceptable excipients. In particular, the present invention relates to novel drug delivery systems of carmustine such as nano-suspension and micro-emulsion and its use for the treatment of cancer by intravenous administration. Also provided are methods for preparation of such novel drug delivery systems.

5 Claims, 4 Drawing Sheets

Figure 1: Tumour regression study of carmustine nano-suspension (Example 3)
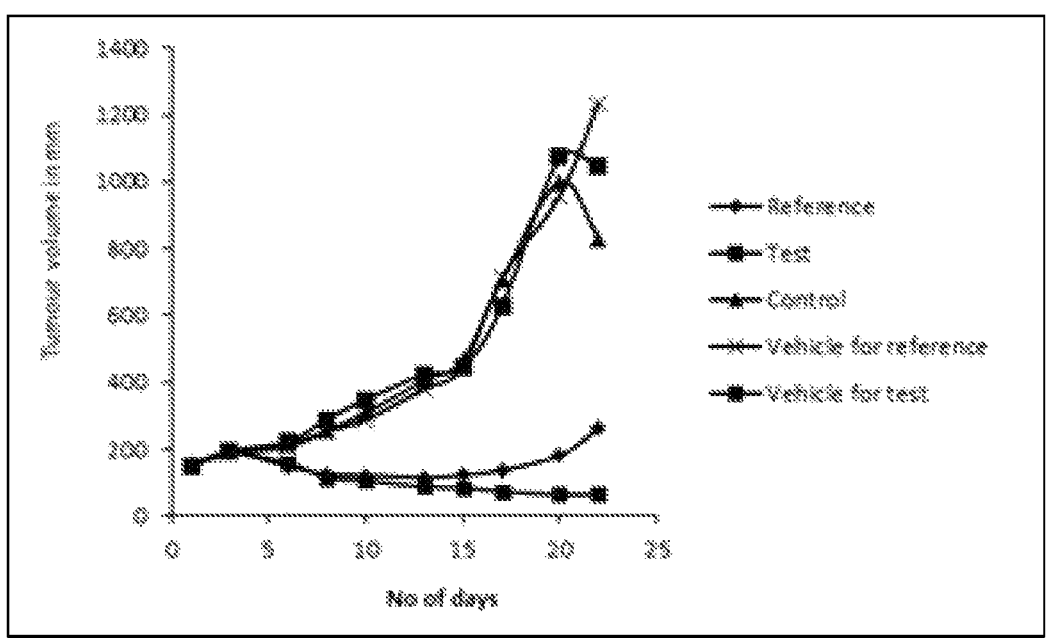

Figure 2: Acute toxicity study (% mortality) of carmustine nano-suspension (Example 3)
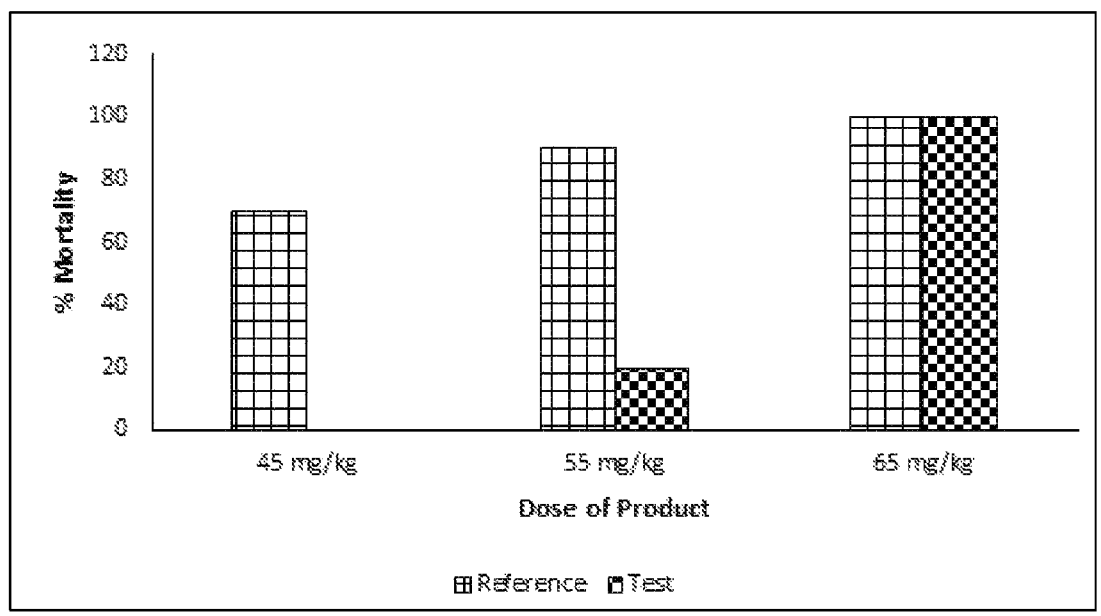

Figure 3: Tumour regression studies of carmustine micro-emulsion (Example 5)
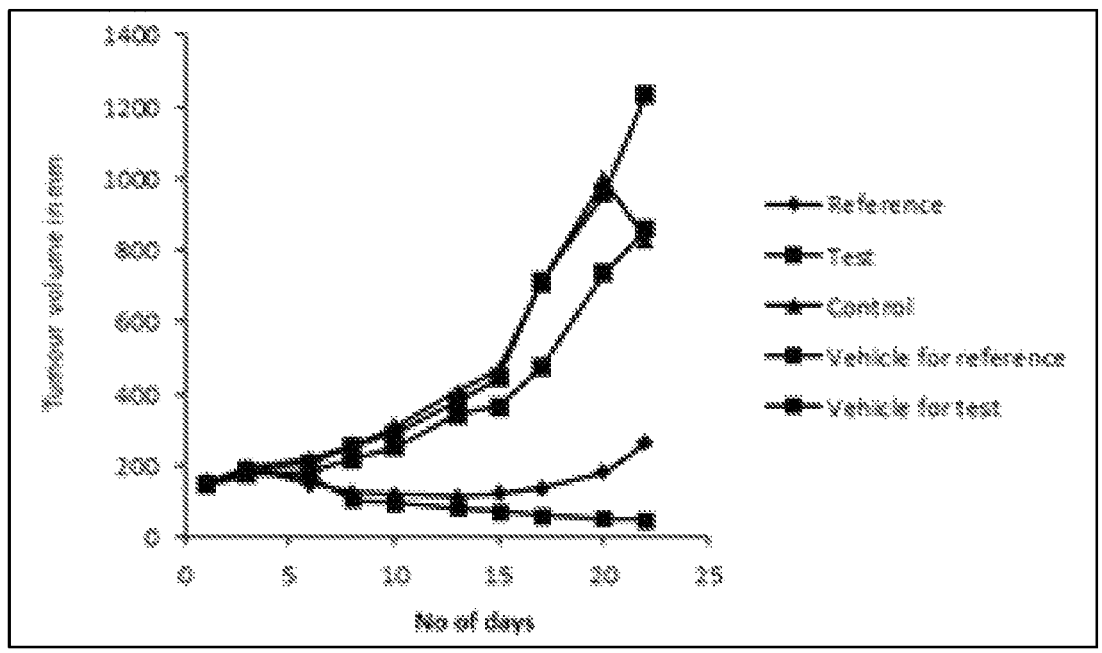

Figure 4: Acute toxicity study (% mortality) of carmustine micro-emulsion (Example 5)
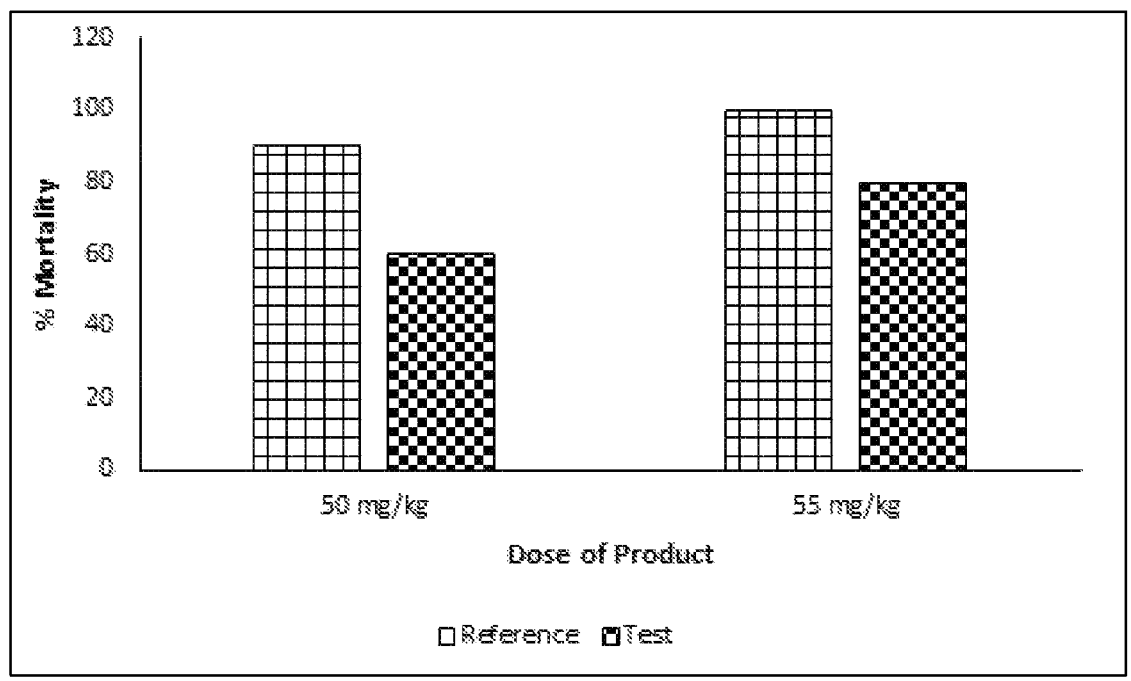

CARMUSTINE FORMULATION

This application is the U.S. National Stage filing of International Patent Application Number PCT/IB2019/052644, filed on Mar. 30, 2019, which claims the benefit of Indian Provisional Application No. IN 201821012964 filed on Apr. 5, 2018, which is are hereby incorporated by reference in its entirety.

FIELD OF THE INVENTION

The present invention relates to a composition comprising nitrosourea and pharmaceutically acceptable excipients. In particular, the present invention relates to novel drug delivery systems of carmustine such as nano-suspension and micro-emulsion and its use for the treatment of cancer by intravenous administration. Also provided are methods for preparation of such novel drug delivery systems.

BACKGROUND OF THE INVENTION

Brain tumor is a mass of unnecessary cells growing in the brain or central spine canal. There are two basic kinds of brain tumors, namely primary brain tumors and metastatic brain tumors. Primary brain tumors initiate and become malignant in the brain. Metastatic brain tumors begin as cancer elsewhere in the body and gradually spread to the brain. Brain tumors are also classified as "benign" or "malignant" based on degree of malignancy or aggressiveness of a brain tumor. Depending on the degree of malignancy, tumors are classified into Grade I, Grade II, Grade III and Grade IV.

According to published reports, nearly 70,000 new cases of primary brain tumors are diagnosed each year and around 10% of these are children between the ages of 0-19. It is reported that brain and central nervous system tumors are the most common cancers among children ages 0-19. There are nearly 700,000 people in the United States living with a brain tumor. There are more than 120 types of brain tumors identified till date.

The main treatments for brain or spinal cord tumors are surgery, radiotherapy and chemotherapy. These treatments are either used alone or in combination. Chemotherapy employs anti-cancer drugs also known as cytotoxic agents to destroy cancer cells. Their therapeutic action is initiated by disrupting the growth of cancer cells. Chemotherapy drugs can be delivered either orally (by mouth as a pill or liquid), intravenously (by infusion into a vein), topically (as a cream on the skin), or through Injection or direct placement (via a lumbar puncture or device placed under the scalp).

Nitrosoureas have been generally utilized as single agent treatment chemotherapy or in established combination therapy with other approved chemotherapeutic agents for many years against primary brain tumors. Nitrosourea includes chemotherapeutic agents such as Chlorozotocin (DCNU), Carmustine (BCNU), Lomustine (CCNU), Nimustine and Ranimustine. Amongst them, Carmustine (bischloroethyl nitrosourea, BCNU or BiCNU) is one of the leading nitrosourea drug for treatment of brain cancers owing to its ability to cross blood-brain barrier and excellent activity against brain tumors.

Carmustine chemically known as 1,3-bis (2-chloroethyl)-1-nitrosourea, alkylates DNA and RNA and interferes with its synthesis and functions. It also binds and modifies (carbamoylates) glutathione reductase, which consequently leads to cell death.

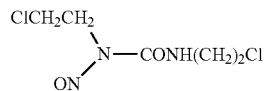

Carmustine is highly soluble in alcohol and lipids but poorly soluble in water wherein it readily gets hydrolyzed in water at pH>6. Carmustine is commercially available as a sterile lyophilized powder for injection under the tradename BiCNU® and in single dose vials containing 100 mg of lyophilized powders of carmustine. Dehydrated alcohol is co-packaged with the active drug product as a sterile diluent for constitution. The lyophilized carmustine appears as a pale yellow dry flake or a dry congealed mass. Prior to injection, the lyophilized carmustine is reconstituted with a co-packed sterile diluent and the solution is then further diluted with sterile water for injection. The reconstitution results in a clear, colorless to yellowish solution which may be further diluted with 5% Dextrose Injection, USP.

Conventional lyophilized formulation of carmustine is associated with frequent and serious toxicity in the form of delayed myelosuppression. Following IV infusion, it is rapidly absorbed by the tissues but is known to be rapidly degraded, with no intact drug detectable after 15 minutes. Therefore, the drug is associated with high toxicity and low selectivity, which in turn reduces the application of this drug for treatment of cancer.

Researchers in the field of formulation have tried to develop various novel drug delivery systems to overcome the limitation associated with the conventional lyophilized formulations.

CN101143130 relates to a parenteral formulation of carmustine in the form of a stable oil-in-water emulsion. The composition comprises of pharmaceutically effective amount of carmustine, oil, a surfactant and water for injection. The invention also discloses the method of preparation of the said oil-in-water emulsion.

CN1110134 discloses an injectable, liposomal formulation and a process for its preparation. The fat-soluble pharmaceutically active ingredient and the liposome matrix are dissolved in an organic solvent to obtain lipid-soluble liquor; or alternatively, only the liposome matrix is dissolved in the organic solvent, and then a water-soluble liquid pharmaceutically active ingredient is added to the lipid-soluble liquor. The organic solvent is then removed from the liquor by using vacuum drying method and then nitrogen gas is charged into it.

Similarly, CN101444482 provides a sustained-release injectable formulation containing a nitrosourea drug, which comprises of sustained-release microspheres and solvents. The sustained-release microspheres each comprise an anti-cancer-active component selected from nitrosourea drugs (such as nimustine and carmustine) and/or topoisomerase inhibitors, and a sustained-release agent.

In order to overcome and/or to reduce such undesired side effects, it was the need of the hour to devise a more efficient drug delivery system which could increase the therapeutic benefit, pharmaceutical efficacy, reduce toxicity with concomitant decrease in side effects. The present invention caters to this long felt need and provides a novel drug delivery system of carmustine for intravenous administration.

SUMMARY OF THE INVENTION

The present invention relates to a composition comprising nitrosourea and pharmaceutically acceptable excipients. In particular, the present invention relates to novel drug delivery systems of carmustine such as nano-suspension and micro-emulsion and its use for the treatment of cancer by intravenous administration. Also provided are methods for preparation of such novel drug delivery systems.

In one embodiment, the present invention relates to a novel drug delivery system comprising carmustine and pharmaceutically acceptable excipients In one of the embodiment the novel drug delivery system of the present invention is in the form of nano-suspension.

In one of the embodiment the nano-suspension of the present invention comprises an organic phase and an aqueous phase, wherein the organic phase further comprises poly (lactic-co-glycolic acid) (PLGA) dissolved in suitable organic solvents and aqueous phase further comprises one or more surfactants dissolved in water for injection.

In one of the embodiment the nano-suspension of the present invention is in the form of lyophilized powder.

In another embodiment the novel drug delivery system of the present invention is in the form of micro-emulsion.

In one of the embodiment the micro-emulsion comprises oil phase and one or more surfactants.

In one of the embodiment the micro-emulsion is in the form of ready-to-use liquid concentrate.

In yet another embodiment, the novel drug delivery systems of the present invention are stable at 2° C. to 8° C. for at least 3 months.

In yet another embodiment, the novel drug delivery systems of the present invention are useful in treatment of a patient suffering from brain tumors, multiple myeloma, Hodgkin's disease, and non-Hodgkin lymphoma.

BRIEF DESCRIPTION OF THE DRAWINGS

FIG. 1 is a graph of the results of a tumour regression study of the carmustine nano-suspension of Example 3.

FIG. 2 is a graph of the results of an acute toxicity study (% mortality) of the carmustine nano-suspension of Example 3.

FIG. 3 is a graph of the results of a tumour regression study of the carmustine micro-emulsion of Example 5.

FIG. 4 is a graph of the results of an acute toxicity study (% mortality) of the carmustine micro-emulsion of Example 5.

DETAILED DESCRIPTION OF THE INVENTION

Novel Drug delivery system (NDDS) is an advanced drug delivery system that utilizes various approaches, formulations and a technology which improves drug potency, controls drug release to give a desired therapeutic effect, provide greater safety and efficacy, and targets a drug specifically to a desired tissue. Combination of advanced techniques results in new dosage forms which are far superior to the conventional dosage forms. Nano-suspension, micro-emulsion, liposomes, neosomes, microcapsules are few examples of the NDDS.

The term nano-suspension as used herein refers to the colloidal dispersion of surface stabilized nanometer sized drug particles. A high concentration of the drug can be incorporated in very small volume of the solvent, which in turn results in the less administration volume. Nano-suspensions can be prepared by high and low energy methods and include high pressure homogenization or ultra-sonication or extrusion or high energy wet milling technique.

The term micro-emulsion as used herein refers to the clear, thermodynamically stable mixtures of oil, water and one or more surfactants. High solubilisation capacity, ease of manufacturing and self-preserving property makes them the composition of choice.

The nano-suspension of the present invention comprises carmustine and a polymer, in which the ratio of the carmustine to the polymer ranges between 1:5 to 1:50.

The amount of carmustine is up to 50% by weight of the composition, preferably about 25% by weight of the composition and more preferably from 0.1 to 10% by weight of the composition.

The amount of biodegradable polymer Poly (lactic-co-glycolic acid) (PLGA) is in the range from 1 to 60% by weight of the composition.

The nano-suspension utilizes one or more organic solvents which form the organic phase, such as acetone, ethyl acetate, ethanol, methanol, dimethyl fumarate, acetonitrile and the like.

Supporting agents/osmotic agents/isotonicity agents which can be used the nano-suspension are selected from but are not limited to mannitol, lactose, glucose, sorbitol, sodium chloride, hydrolyzed gelatin, dextran, sucrose, glycine, polyvinylpyrrolidone and the like. Typically, sucrose is the preferred osmotic agent, employed in the present formulation.

Typically, nano-suspension of the present invention is provided as a lyophilized powder suitable for dilution.

Suitable freeze drying excipients or cryoprotectants in the nano-suspension include but not limited to mannitol, trehalose, sorbitol, sucrose and the like.

Reconstitution of the carmustine nano-suspension lyophilized powder can be carried out with suitable aqueous solvents selected from WFI, dextrose, saline and the like.

A typical process for manufacture of the nano-suspension composition of Carmustine according to the present invention comprises of:
1. Dissolving required quantity of polymer in organic solvent with stirring
2. Adding carmustine to the solution of step 1;
3. Separately a surfactant was dissolved in water for injection (WFI). Other water soluble excipients, if required, may be added in the solution.
4. The carmustine solution was added to the surfactant solution with stirring in about 30 minutes.
5. The solvent was evaporated by nitrogen purging on surface.
6. The required volume was made up by adding WFI and optionally the mixture was dialyzed.
7. The solution was lyophilized and packed in suitable container closure system.

During manufacturing of nano-suspension, suitable mixers and homogenizers are used to achieve uniform dispersion. Typically, solution is homogenized at pressure range up to 20000 psi to achieve desired particle size (less than 300 nm). During this process, temperature is controlled and kept at about 5° C. Lyophilisation was carried out by the conventional process known in the art.

Modification in the above mentioned process to achieve the optimum drug entrapment can be made as known to the person skilled in the art.

In another preferred embodiment, the present invention provides carmustine formulation in the form of micro-emulsion.

The micro-emulsion of the present invention is in the form of ready-to-use liquid concentrate and comprises oil phase and one or more surfactants, optionally with other pharmaceutically acceptable excipients.

The oil phase as utilized in the micro-emulsified drug formulation according to the present invention is a phase that is capable of dissolving and/or suspending carmustine and capable of forming nano-emulsion when diluted with an aqueous phase. Thus, this can be literally any fatty acid, triglyceride etc. An oil or fat ingredient may be any of an oil or fat in a liquid state at room temperature, an oil or fat in a solid state at room temperature, and a mixture thereof. An oil or fat may include at least one selected from a monoglyceride, a diglyceride and a triglyceride.

The oily phase could be present in concentration of up to 50% by weight of the composition; preferably it is up to 40% by weight of the composition, preferably it is up to 30% by weight of the composition.

Typically, oils include fats, fat-derived materials and lipids that are relatively insoluble in water but soluble in organic solvents, are related either actually or potentially to fatty acid esters, fatty alcohols, sterols, waxes, or the like, and are utilizable by the animal organism. The oil or fat may be selected from but not limited to olive oil, camellia oil, macadamia nut oil, castor oil, avocado oil, evening primrose oil, turtle oil, corn oil, mink oil, rapeseed oil, egg yolk oil, sesame oil, persic oil, wheat germ oil, sasanqua oil, linseed oil, safflower oil, cotton seed oil, perilla oil, soybean oil, peanut oil, tea seed oil, kaya oil, rice bran oil, china wood oil, tung oil, jojoba oil, germ oil, glycerin trioctanoate, glycerin triisopalmitate, salad oil, safflower oil (Carthamus tinctorius oil), palm oil, coconut oil, peanut oil, almond oil, hazelnut oil, walnut oil, and grape seed oil, Propylene glycol dicaprylocaprate (Labrafac® PG), linoleoyl Polyoxyl-6 glycerides (Labrafil M2125), Oleoyl polyoxyl-6 glycerides (Labrafil M1944), caprylic/capric glyceride units cross-linked with succinic acid (Miglyol).

Typically, lipid can comprise a blend of triglycerides as commercially available under the brand name SOFTISAN®. For example, the lipid can comprise the commercially available SOFTISAN® 100, SOFTISAN 133, SOFTISAN 134, SOFTISAN 138, SOFTISAN® 142, SOFTISAN® 154, or a blend thereof. In a still further aspect, the lipid can comprise a blend of triglycerides as commercially available under the brand name WITEPSOL H35®, and SOFTISAN 133®, SOFTISAN 134®, SOFTISAN 138®, SOFTISAN 378®, SOFTISAN 601®, and/or SOFTISAN 767®. In one aspect, the lipid can comprise fatty acid include palmitic, stearic, arachidic, behenic, or lignoceric acid. Preferred fatty acids include palmitic, stearic, arachidic, behenic acid.

The present invention also provides a process for manufacture of micro-emulsion formulation of carmustine for parenteral administration. The desired amount of carmustine is dissolved in oil phase and then other excipients such as one or more surfactants are added to get dispersion and packaged in the suitable container.

Modifications in the above mentioned process can be made as known to the person skilled in the art The primary role of the surfactant is for stabilization of the nanoparticles in the colloidal state and prevention of particle size growth during storage. The choice of surfactants is an important parameter to be considered in optimizing any nanoparticle formulation, not only to control the particle size and stabilization of the dispersions but also to control the crystallization and polymorphic transitions. One or more surfactants which can be used in the nano-suspension and micro-emulsion compositions according to the present invention comprise hydrophilic surfactants and hydrophobic surfactants and include, but not limited to Polysorbates (Tween™), sodium cholesteryl sulfate (SCS), Sodium dodecyl sulfate, sodium lauryl sulfate, Lauryl dimethyl amine oxide, Cetyltrimethylammonium bromide (CTAB), Polyethoxylated alcohols, Polyoxyethylene sorbitan, Octoxynol (Triton X100™), N, N-dimethyldodecylamine-N-oxide, Hexadecyltrimethylammonium bromide (HTAB), Polyoxyl 10 lauryl ether, Brij 721™, Bile salts (sodium deoxycholate, sodium cholate), Polyoxyl castor oil (Cremophor™), Polyethylene glycol 35 castor oil (PEG-35 castor oil), Polyethylene glycol 400 (PEG-400), Nonylphenol ethoxylate (Tergitol™), Cyclodextrins, Lecithin, Methylbenzethonium chloride (Hyamine™), Polyglyceryl-3-Dioleate (Plurol® Oleique CC 497 CG), Polysorbate 20, Transcutol HP, Egg Phosphatidylcholine, Soybean Phosphatidylcholine (SPC90G), Non-GMO Phosphatidylcholine, Hydrogenated Phosphatidylcholine and Synthetic Phosphatidylcholine and the like.

The amount of surfactant in nano-suspension or micro-emulsion formulations of present invention is in the range from 1 to 70% by weight of the composition, preferably from 1 to 60% by weight of the composition, preferably from 1 to 50% by weight of the composition, preferably from 1 to 40% by weight of the composition.

Further, other conventional adjutants such as, antimicrobial preservatives, Buffering/pH adjusting agents, stabilizers/antioxidants, etc. are also employed in the preparation of novel drug delivery systems of the present invention.

Preservatives may be selected from but not limited to alpha-tocopherol, phenol, cresol, tri-butanol, benzyl alcohol, and paraben.

Buffering/pH adjusting agents according to present invention include, but are not limited to a mineral acid or an organic acid like hydrochloric acid, citric acid, tartaric acid, phosphoric acid, meta-phosphoric acid, poly-meta-phosphoric acid, carbonic acid or a base (organic/inorganic) like sodium hydroxide, potassium hydroxide, sodium citrate, potassium citrate, sodium bicarbonate potassium carbonate, amine, disodium hydrogen phosphate, dipotassium hydrogen phosphate, disodium succinate hexahydrate, monoethanolamine, diethanolamine, triethanolamine, 1,2-hexanediamine, sodium carbonate, sodium potassium tartrate, potassium metaphosphate, polyvinylidene potassium phosphate, sodium metaphosphate one or several. Preferably, the pH of the pharmaceutical composition of the present invention is 8 or less, preferably a pH of 5.6±2.

Stabilizers/antioxidants to be used in present invention may be selected from, but not limited to, sodium sulfite, sodium bisulfite, sodium metabisulfite, sodium thiosulfate, thiourea, vitamin C, butylated hydroxy anisole, dibutyl phenol, propyl gallate, tocopherol, methionine, cysteine hydrochloride, acetyl cysteine, N-acetyl-DL-methionine, ascorbic palmitate, ethylenediaminetetraacetic acid, disodium edetate etc.

Phase volume ratio (ratio of dispersed phase to continuous phase), surface characteristics (e.g. surface charge), entrapment efficacy, and particle size of the dispersed phase were found to be important factors in determining the stability of the composition of invention, pharmacokinetics of drug administered in suspension and final efficacy of the product.

Before administration to patients, the formulation according to the present invention may further comprise one or more pharmaceutically acceptable vehicle carriers therein. Such carriers may be selected from saline, sterile water, Ringer's solution, buffered saline, dextrose solution, maltodextrin solution, glycerol, ethanol and a combination thereof.

The novel drug delivery system may be in the form of injections such as suspensions, emulsions, or injectable form of freeze-dried powder ready for reconstitution.

The ready-to-use liquid concentrate micro-emulsion after dilution with a suitable aqueous vehicle at the time of administration gets converted to nano-emulsion.

Depending on the nature and purpose, the preparation according to the present invention may be administered parenterally by intravenous, subcutaneous, intrathecal or intraperitoneal. The dose of the nano-suspension and micro-emulsion of present invention may vary depending on various factors including the weight, age, gender, and the state of health of the patients as well as on the diet, time of administration, route of administration, rate of excrement, and severity of illness.

According to present invention, said pharmaceutical preparation is stable; wherein "stable pharmaceutical preparation" is defined as no aggregation is observed when said pharmaceutical preparation is kept for stability studies at 2° C. to 8° C. (Real time study) for at least 3 months and wherein the assay of carmustine was at least 90%. Further the carmustine composition contains not more than about 0.5% of carmustine impurity A and the total known and unknown impurities in the present composition are less than about 1.0% by weight.

The assay of carmustine in the said pharmaceutical preparation can be carried out by any of the methods known to the person skilled in the art, e.g. High performance liquid chromatography (HPLC), Spectrophotometry (UV spectrophotometry), Gas Chromatography (GC) etc.

Carmustine novel drug delivery systems of the present invention are useful for the treatment of brain tumors (glioblastoma, brainstem glioma, a medulloblastoma, astrocytoma, and room ependymoma), brain metastases and meningeal leukemia. It can also be used to treat malignant lymphoma, multiple myeloma, or in combination with other drugs for treatment of malignant melanoma.

The safety and efficacy studies (tumor regression, % mortality and acute toxicity) of nano-suspension and micro-emulsion formulations of present invention were performed in animals. The study protocols and results are presented in examples listed below.

Both nano-suspension and micro-emulsion compositions of the present invention were found to be stable over the entire stability period (3 months) at 2-8° C. (Real time study) as total impurities were within the prescribed limits of less than about 1.0% by weight.

In tumour regression study, for nano-suspension compositions tumour volume was found to be decreased considerably at the end of 20$^{th}$ day and was further maintained till completion of the study (22 days) and for micro-emulsion compositions tumour volume was found to be decreased considerably till completion of the study (22 days). On the contrary, in reference product (BiCNU) the tumour volume was substantially increased after 13$^{th}$ day.

In acute toxicity studies, % mortality was reduced moderately, confirming the safety of the nano-suspension composition at 45 mg/Kg and 55 mg/Kg dosage strength and micro-emulsion composition at 50 mg/Kg and 55 mg/Kg dosage strength; as compared to reference product (BiCNU).

A better understanding of present invention may be obtained through the following examples and process for manufacturing set forth to illustrate, but should not be construed as limiting the present invention.

EXAMPLES

Various carmustine nano-suspension formulations were made by using the formulae as summarized in below Examples 1 to 4:

Example 1 and 2: Preparation of Carmustine Nano-Suspension for Injection

| Composition | Example 1 mg/gm | Example 2 mg/gm |
|---|---|---|
| Organic Phase | | |
| Carmustine | 2.00 | 1.00 |
| Poly (D,L-lactic-co-glycolic acid) (PLGA) | 10.00 | 5.00 |
| Acetone | qs | qs |
| Methanol | qs | qs |
| Aqueous Phase | | |
| Polysorbate 20 | 13.00 | 6.50 |
| Water for Injection (WFI) | qs | qs |

Above formulations were prepared by a typical process comprising following steps:
1. Initially, required quantity of methanol & acetone was mixed to prepare organic phase
2. Poly (lactic-co-glycolic acid) (PLGA) was dissolved in this acetone-methanol mixture by continuous stirring method
3. Carmustine was dissolved in solution from step 2 under stirring
4. Separately, Polysorbate 20 solution was prepared by using water for injection (WFI).
5. Solution containing carmustine and polymer was mixed with polysorbate solution and the resultant solution was stirred for at least 30 min
6. Solvents were evaporated.
7. The final volume was adjusted using WFI.
8. Measured volume of the solution was then filled in suitable vials and lyophilized

Example 3 and 4: Preparation of Carmustine Nano-Suspension for Injection

| Sr. No | Ingredients | Example 3 mg/gm | Example 4 mg/gm |
|---|---|---|---|
| Organic phase | | | |
| 1 | Carmustine | 10.00 | 5.00 |
| 2 | Poly(D,L-lactide-co-glycolide) (PLGA) | 30.00 | 30.00 |
| 3 | Acetone | 0.69 | 0.69 |
| 4 | Methanol | 0.1 | 0.1 |
| Aqueous phase | | | |
| 1 | Soybean Phosphatidylcholine (SPC90G) | 30.00 | 30.00 |
| 2 | Sodium cholesteryl sulfate (SCS) | 1.2 | 1.2 |
| 3 | Sucrose | 80.00 | 80.00 |
| 4 | WFI | 848.7 | 853.8 |

The brief procedure used to prepare these formulations was as follows:

1. Poly D,L-lactide-co-glycolide) (PLGA) was dissolved in required quantity of acetone under stirring. Methanol was added to this solution.
2. Carmustine was dissolved in solution from step 1 under stirring,
3. In a separate vessel, Soybean Phosphatidylcholine (SPC90G) and sodium cholesteryl sulfate (SCS) were added to WFI (80% of batch size) under stirring. This composition was subjected to high speed homogenization at 10000 PSI for 15 min.
4. High pressure homogenization was continued at 18000 PSI till desired size was achieved.
5. Weighed quantity of sucrose was dissolved in the composition solution of step 4 and final volume was made up with WFI,
6. Above step 5 composition was added to step 2 solution with continuous stirring for 30 min.
7. Later, solvents of step were evaporated by compressed air blanketing.
8. Final composition in step 7 was optionally lyophilized.

Stability Studies:

Stability studies of nano-suspension composition were carried out at 2-8° C. (Real time study). The measurement of assay, % entrapment efficiency and presence of total impurities were evaluated after 1, 2 and 3 months of storage.

The compositions were found to be stable over the entire stability period (Table 3). Total impurities were also within the prescribed limits confirming the stability of the nano-suspension composition.

TABLE 3

Stability studies results of carmustine nano-suspension (Example 3)

| Test | Carmustine Nano-suspension Injection stability | | | |
|---|---|---|---|---|
| | Initial | 1 month 2-8° C. | 2 month 2-8° C. | 3 month 2-8° C. |
| Assay | 96.00% | 95.10% | 93.80% | 95.50% |
| Drug Entrapped | 58.90% | | | |
| | Related substance | | | |
| Impurity A | 0.087% | 0.120% | ND | 0.030% |
| Single max unknown impurity | 0.172% | 0.027% | 0.010% | 0.039% |
| Total impurities | 0.568% | 0.167% | 0.024% | 0.088% |

Tumour Regression Study of Carmustine Nano-Suspension:

Tumours were induced in SCID Beige mice by inoculation of U-87 MG cell line by subcutaneously injecting/implanting 0.1 ml of the cell suspension with appropriate cell numbers (approximately 5×10⁶ cells) in the right side flank area. Tumors were allowed to grow to the appropriate size (average tumour volumes around 100 mm) before commencement of the treatment regimen. Tumour volume was measured at least 3 times a week using digital caliper after tumour induction.

Reference and Test formulations (10 ml/Kg body weight) were administered to animals by intravenous route (through tail vein). Dosing was done once a week for four weeks from day 1 of treatment period.

Tumours decreasing in weight during treatment were assessed for partial or complete regression. Complete regressions were defined by instances in which the tumour volume falls below measurable limits (less than 63 mg; tumour density 1 mm3=1 mg) but again grows before the end of the experiment.

TABLE 4

Tumour regression study of carmustine nano-suspension (Example 3)
Tumour Regression Study

| Formulation | Mortality | Mean Tumour volume at specific days (mm) | | | | | | | | | |
|---|---|---|---|---|---|---|---|---|---|---|---|
| | | 1 | 3 | 6 | 8 | 10 | 13 | 15 | 17 | 20 | 22 |
| Reference | 07/10 | 150 | 189.4 | 146.6 | 123.8 | 119.8 | 113.8 | 120.3 | 136 | 180.2 | 261.8 |
| Test | 02/10 | 147.7 | 190.4 | 157.5 | 113.1 | 103.9 | 86.2 | 82.3 | 72.9 | 63 | 64.6 |
| Control | 03/10 | 151.7 | 195.3 | 217.3 | 256.1 | 308.2 | 405.1 | 465.7 | 706.9 | 998.7 | 832.1 |
| Vehicle for reference | 02/08 | 147.5 | 184.6 | 207.5 | 252.3 | 287.9 | 379.9 | 443.9 | 712.2 | 957.4 | 1235.0 |
| Vehicle for test | 03/08 | 146.2 | 193.2 | 222.6 | 289.3 | 347.8 | 423.0 | 443.8 | 625.3 | 1072.5 | 1044.3 |

The results of the experiment are presented in Table 4. The intravenous administration of reference and test formulations resulted in a substantial tumour regression (FIG. 1). The regression effect was maintained for the whole duration of the experiment (22 days) in case of test sample. However, tumours treated with reference sample started re-growing after day 13. Significant difference was also observed in the mortality rate throughout the study period confirming safety of the nano-suspension composition.

Acute Toxicity Study of Carmustine Nano-Suspension:

Acute toxicity study of reference and test formulations of carmustine was carried out by intravenous (tail vein) administration of 45, 55 & 65 mg/kg body weight of carmustine formulations to Swiss Albino mice in the respective groups. Dose volume was not more than 20 ml/Kg. All mice were observed for any signs of toxicity at 0.5 h, 1 h, 2 h, 4 h, 6 h and 24 h after completion of dosing and thereafter daily twice for mortality during the observation period (14 days). All treated live animals were euthanized on day 15 using carbon dioxide gas or thiopentone sodium injection administered intraperitoneally (80-90 mg/animal).

TABLE 5

Acute toxicity study of carmustine nano-suspension (Example 3)
Acute toxicity study

| Formulation | % Mortality | | |
|---|---|---|---|
| | 45 mg/kg | 55 mg/kg | 65 mg/kg |
| Reference: BiCNU (RLD) | 70 | 90 | 100 |
| Test: (PLGA Nano-suspension) | 0 | 20 | 100 |

Study results (Table 5) showed that there was significant difference in % mortality between the test and reference group at different dose range. At 45 & 55 mg/kg body weight dose, the test formulation was found to be extremely safe than the reference sample (FIG. 2). At 65 mg/kg body weight dose, the rats died within 14 days after treatment for both the reference and the test sample.

Various carmustine micro-emulsion formulations were made by using formulae as summarized in below Examples 5 to 8.

Example 5 to 8: Preparation of Carmustine Micro-Emulsion for Injection

| Ingredients | Example 5 mg/gm | Example 6 mg/gm | Example 7 mg/gm | Example 8 mg/gm |
|---|---|---|---|---|
| Carmustine | 100.0 | 100.0 | 100.0 | 100.0 |
| Caprylic/Capric Triglyceride (Miglyol) | 300.00 | — | — | — |
| Propylene glycol dicaprylocaprate (Labrafac PG) | — | — | — | 300.00 |
| Oleoyl polyoxyl-6 glycerides (Labrafil M 1944) | — | 300.00 | — | — |

-continued

| Ingredients | Example 5 mg/gm | Example 6 mg/gm | Example 7 mg/gm | Example 8 mg/gm |
|---|---|---|---|---|
| Linoleoyl Polyoxyl-6 glycerides (Labrafil M 2125CS) | — | — | 300.00 | — |
| PEG-35 castor oil | 466.00 | 466.00 | 466.00 | 466.00 |
| Polyglyceryl-3 dioleate (Plurol oleique CC 497) | 233.00 | — | — | — |
| Polyethylene Glycol-400 (PEG-400) | — | 233.00 | 233.00 | — |
| Diethylene glycol monoethyl ether (Transcutol HP) | — | — | — | 233.00 |

Above described composition was prepared by dissolving carmustine in required quantity of oil with stirring. After complete dissolution, surfactant was added and stirred till clear dispersion is obtained. The samples were evaluated for stability at pharmaceutically acceptable conditions of stability testing and were found to meet all the requirements.

Stability Studies of Carmustine Micro-Emulsion:

Stability studies of micro-emulsion composition were carried out at 2-8° C. (Real time study). The measurement of assay and presence of total impurities were evaluated after 1, 2 and 3 months of storage.

Data from the stability studies indicated that the total impurities were within the prescribed limits confirming the stability of the micro-emulsion compositions.

TABLE 7

Stability studies results of carmustine micro-emulsion (Example 5) Carmustine Micro-emulsion Injection

| Test | Initial | 1 month 2-8° C. | 2 month 2-8° C. | 3 month 2-8° C. |
|---|---|---|---|---|
| Assay | 105.90% | 105.50% | 103.10% | 99.20% |
| Related substance | | | | |
| Impurity A | 0.168% | 0.167% | 0.195% | 0.275% |
| Single max unknown impurity | 0.256% | 0.259% | 0.451% | 0.395% |
| Total impurities | 0.822% | 0.976% | 1.086% | 1.289% |

Tumour Regression Study of Carmustine Micro-Emulsion:

Tumour regression studies of micro-emulsion formulations were performed in the same manner as described above for the nano-suspension formulations.

TABLE 8

Tumour regression study of carmustine micro-emulsion (Example 5) Tumour Regression Study Data

| Formulation | Mortality | Mean Tumour volume at specific days (mm) | | | | | | | | | |
|---|---|---|---|---|---|---|---|---|---|---|---|
| | | 1 | 3 | 6 | 8 | 10 | 13 | 15 | 17 | 20 | 22 |
| Reference | 07/10 | 150 | 189.4 | 146.6 | 123.8 | 119.8 | 113.8 | 120.3 | 136 | 180.2 | 261.8 |
| Test | 02/10 | 147.3 | 185.2 | 164.1 | 105.3 | 94.3 | 80.1 | 73.2 | 59.7 | 51.8 | 47.5 |
| Control | 03/10 | 151.7 | 195.3 | 217.3 | 256.1 | 308.2 | 405.1 | 465.7 | 706.9 | 998.7 | 832.1 |
| Vehicle for reference | 02/08 | 147.5 | 184.6 | 207.5 | 252.3 | 287.9 | 379.9 | 443.9 | 712.2 | 957.4 | 1235.0 |
| Vehicle for test | 05/08 | 144.7 | 173.7 | 183.7 | 219.3 | 250.8 | 339.9 | 364.1 | 472.6 | 735.2 | 858.0 |

The results of the experiment are presented in Table 8. The intravenous administration of reference and test formulations resulted in the substantial tumour regression (FIG. 3). The regression effect was maintained for the whole duration of the experiment (22 days) in case of test sample. However, tumours treated with reference sample started re-growing after day 13. Significant difference was also observed in the mortality rate throughout the study period confirming safety of the micro-emulsion composition.

Acute Toxicity Study (% Mortality) of Carmustine Micro-Emulsion:

Only two dose strengths (50 mg/kg & 55 mg/kg) were evaluated in case of micro-emulsion composition as 100% mortality was observed at 65 mg/kg dose strength in case of reference and test nano-suspension composition in earlier studies.

Study results (Table 9) showed that both reference and test samples are comparable with each other as there was not much difference in the mortality rate for both the tested dosage strengths (FIG. 4).

TABLE 9

Acute toxicity study of carmustine micro-emulsion (Example 5)
Acute toxicity study

| Formulation | % Mortality | |
|---|---|---|
| | 50 mg/kg | 55 mg/kg |
| Reference: BiCNU (RLD) | 90 | 100 |
| Test: (Micro-emulsion) | 60 | 80 |

We claim:

1. A drug composition comprising: (i) 0.1 wt % to 50 wt % of carmustine: (ii) 1 wt % to 70 wt % of a combination of phosphatidylcholine and sodium cholesteryl sulfate: (iii) 1 wt % to 60 wt % of poly (lactic-co-glycolic acid) (PLGA): (iv) sucrose and (v) water wherein the ratio of carmustine to PLGA ranges from 1:3 to 1:6 weight-per-weight (w/w) and the composition is a nano-suspension.

2. A lyophilized powder obtained by lyophilizing the drugs composition of claim 1.

3. The drug composition of claim 1 wherein the phosphatidylcholine is soybean phosphatidylcholine.

4. The drug composition of claim 1 comprising: (i) 0.1 wt % to 10 wt % carmustine; and (ii) 1 wt % to 40 wt % of the phosphatidylcholine and sodium cholesteryl sulfate combination.

5. A method for treating brain tumors, brain metastases, meningeal leukemia, malignant lymphoma or multiple myeloma comprising (a) combining an effective amount of the lyophilized powder according to claim 2 with a carrier selected from saline, sterile water, Ringer's solution, buffered saline, dextrose solution, maltodextrin solution, glycerol, ethanol and a combination thereof and (b) parenterally administering the combination of step (a) to a patient with a brain tumor, brain metastases, meningeal leukemia, malignant lymphoma or multiple myeloma.

* * * * *